(12) United States Patent
Kyriakou

(10) Patent No.: US 10,726,549 B2
(45) Date of Patent: Jul. 28, 2020

(54) AUTOMATED INTENSITY ADAPTATION IN FLUOROSCOPY

(71) Applicant: Siemens Healthcare GmbH, Erlangen (DE)

(72) Inventor: Yiannis Kyriakou, Spardorf (DE)

(73) Assignee: Siemens Healthcare GmbH, Erlangen (DE)

(*) Notice: Subject to any disclaimer, the term of this patent is extended or adjusted under 35 U.S.C. 154(b) by 146 days.

(21) Appl. No.: 16/032,377

(22) Filed: Jul. 11, 2018

(65) Prior Publication Data
US 2019/0019288 A1  Jan. 17, 2019

(30) Foreign Application Priority Data
Jul. 11, 2017 (EP) .................................. 17180773

(51) Int. Cl.
| | | |
|---|---|---|
| *A61B 6/00* | (2006.01) | |
| *G06T 5/50* | (2006.01) | |
| *A61B 6/12* | (2006.01) | |
| *G06T 7/00* | (2017.01) | |
| *G06T 7/136* | (2017.01) | |
| *G06T 7/11* | (2017.01) | |

(52) U.S. Cl.
CPC ............. *G06T 7/0012* (2013.01); *A61B 6/12* (2013.01); *A61B 6/4441* (2013.01); *A61B 6/481* (2013.01); *A61B 6/487* (2013.01); *A61B 6/5205* (2013.01); *A61B 6/5235* (2013.01); *G06T 5/50* (2013.01); *G06T 7/11* (2017.01); *G06T 7/136* (2017.01); *G06T 7/97* (2017.01); *G06T 2207/10121* (2013.01); *G06T 2207/20221* (2013.01); *G06T 2207/30101* (2013.01)

(58) Field of Classification Search
None
See application file for complete search history.

(56) References Cited

U.S. PATENT DOCUMENTS

| | | | |
|---|---|---|---|
| 2005/0089143 A1 | 4/2005 | Nakano et al. | |
| 2009/0279767 A1* | 11/2009 | Kukuk ..................... | G06T 7/74 382/132 |

(Continued)

OTHER PUBLICATIONS

European Search Report for European Patent Application No. 17180773.8-1124 dated Jan. 25, 2018.

*Primary Examiner* — Idowu O Osifade
(74) *Attorney, Agent, or Firm* — Lempia Summerfield Katz LLC

(57) ABSTRACT

Operating a medical X-ray apparatus to create a fluoroscopy includes capturing a first X-ray image of a vascular tree as a vascular mask, and segmenting the first X-ray image into at least one image area with the vascular tree and at least one image area without the vascular tree. An intensity of the first X-ray image for the image area with the vascular tree is ascertained as a vascular mask intensity. A second X-ray image of a medical component introduced into the vascular tree is created as a component image. An intensity of the second X-ray image for an image area with the medical component is ascertained as a component intensity. A ratio of component intensity and vascular tree intensity is calculated, and an overlay image with the first and the second X-ray image is generated depending on the calculated ratio of the vascular mask intensity and the component intensity.

13 Claims, 1 Drawing Sheet

(56) References Cited

U.S. PATENT DOCUMENTS

2011/0038458 A1    2/2011  Spahn
2011/0235889 A1*   9/2011  Spahn .................. A61B 6/4441
                                                       382/132

* cited by examiner

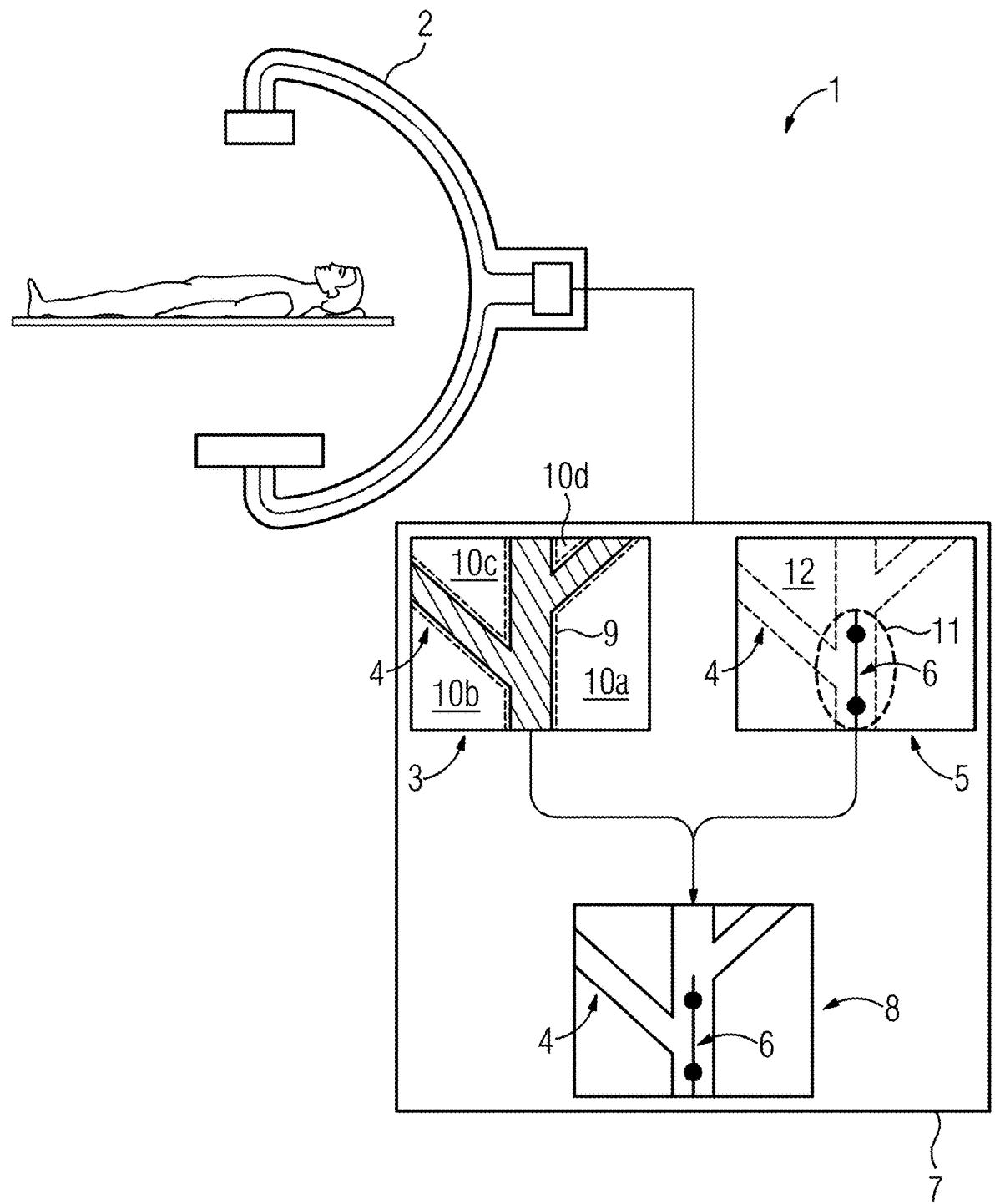

AUTOMATED INTENSITY ADAPTATION IN FLUOROSCOPY

This application claims the benefit of EP 17180773.8, filed on Jul. 11, 2017, which is hereby incorporated by reference in its entirety.

BACKGROUND

The present embodiments relate to creating a fluoroscopy.

Within the interventional radiology and/or oncology, the primary imaging is effected using X-radiation, for example, by capturing or acquiring a two-dimensional real-time fluoroscopy (e.g., 2D live fluoroscopy). Therein, a special method of fluoroscopy is the "roadmap mode". Therein, a medical component, a "device" such as a wire, a catheter, or a stent (e.g., an X-ray image of this component) is overlaid on a previously captured vascular mask in real-time imaging. Therein, the overlaid component (e.g., the component image overlaid with the vascular mask) may be referred to as an overlay image. This overlay image is used in real-time imaging as a navigation aid to avoid multiple contrast agent injections and additional captures or X-ray recordings.

Therein, the dark component is usually overlaid with a brightly displayed vascular mask. Typically, the vascular mask and the component image are therein overlaid in a mixing method and, for example, linearly weighted. Therein, the images are mixed as a whole, which basically functions well if the contrast ratio, thus the respective intensities of the differently overlaid images, are manually adapted to the respective situation.

The adaptation requirement results from the fact that the vascular mask and corresponding contrast to the background vary (e.g., over different injection types and injection locations). This results in different representation of the medical component in the final mixed image. Therein, the manual adaptation of the contrast, thus the manual adaptation of the intensities (e.g., image intensities) of the images overlaid in the overlay image in an image area with the vascular tree and in an image area with the medical component, is not always desired by the respective operator and may also be limited by boundaries of the adjustment parameters. Thus, in some circumstances, the ideal contrast or the ideal intensity ratio of the mentioned intensities may not be achieved. Correspondingly, variations in the contrast may occur in the overlay image, which may be annoying for the operator and disadvantageous for the process of the medical intervention.

SUMMARY AND DESCRIPTION

The scope of the present invention is defined solely by the appended claims and is not affected to any degree by the statements within this summary.

The present embodiments may obviate one or more of the drawbacks or limitations in the related art. For example, a fluoroscopy with improved contrast is obtained.

An aspect relates to a method for operating a medical X-ray apparatus in or while creating a fluoroscopy. The medical X-ray apparatus may, for example, be a C-arm X-ray apparatus, or the medical X-ray apparatus may include such an apparatus. However, the method described below is basically applicable to all imaging modalities based on X-ray.

Therein, the method includes a series of method acts. One method act is capturing a first X-ray image of a vascular tree of a patient as a vascular mask. Thus, the first X-ray image serves as a vascular mask or is suitable for such a use in the further method as known from the prior art. A further method act is segmenting the first X-ray image into at least one image area with the vascular tree and at least one further image area without the vascular tree. Therein, segmenting may include or be segmenting based on a threshold value. Segmenting serves for identifying the image areas, in which a contrast agent or correspondingly the vascular tree was or is. A further method act is ascertaining or determining an intensity of the first X-ray image for the image area with the vascular tree as a vascular mask intensity. The vascular mask intensity may differ from the intensity of the image area without vascular tree and generally will also be different from it (which substantiates the advantages of the proposed method).

A further method act is creating a second X-ray image of a medical component introduced into the vascular tree as a component image ("device image"). The component image may, for example, be generated by subtraction of a real-time X-ray image and a previously captured anatomic mask as known from the prior art. The creation of the second X-ray image may therefore include subtraction of a captured real-time fluoroscopy image with a recorded or stored X-ray image previously captured as an anatomic mask. Therein, the anatomic mask serves for deleting bones and further features not interesting for the respective intervention in the captured area of the patient as generally known. Thus, ideally, an image arises as the component image, in which only the medical component introduced into the patient or into the vascular tree is visible. However, in reality, situation artifacts arise here by movement, an anatomy slightly altered with respect to the anatomic mask, X-ray parameters, noise and so on. These are all factors that aggravate easy segmenting out or identification of the medical component.

A further method act is segmenting (e.g., based on a threshold value) the second X-ray image into an image area with the medical component and an image area without the medical component. Ascertaining or determining an intensity of the second X-ray image for the image area with the medical component as a component intensity follows. Therein, the component intensity may differ from the intensity of the image area without medical component and generally will also be different from it (which substantiates the advantages of the proposed method).

A further method act is calculating a ratio of component intensity and vascular tree intensity (e.g., a component-to-vascular-tree intensity or a vascular-tree-to-component intensity). Generating an overlay image with the vascular tree and the medical component (e.g., thus an overlay image, in which the vascular tree and the medical component are imaged) is effected with the first X-ray image and the second X-ray image depending on the calculated ratio of the vascular mask intensity and the component intensity such that the intensity of the overlay image in an image area with the vascular tree and the intensity of the overlay image in an image area with the component are in a preset or presettable ratio (e.g., a target ratio).

Thus, the method of one or more of the present embodiments realizes automatic adaptation or optimization of the contrast between vascular tree and medical component in the overlay image. Therein, this optimum contrast may be defined in advance before generating the overlay image by ascertaining or determining the intensity of the image area of the vascular mask interesting for an operator (e.g., the intensity of the image area with the vascular tree in the first X-ray image) and the intensity in the area of the component image interesting for the operator (e.g., the intensity of the image area with the medical component in the second X-ray image), respectively, independently of each other. Thus, for the overlay image, the optimum contrast is not respectively averaged over the respective X-ray images, the vascular mask and the component image as a whole, but only the respective characteristic specifically interesting for the overlay image, the intensity, of the respective image areas relevant to the overlay image are examined and considered. Thereto, the vascular mask as such, thus without the component image, is considered, and an intensity analysis is performed for the vascular tree. For this analysis or this ascertainment of the intensity, the vascular mask may be inverted in a gray value distribution so as to realize the usual final vascular mask representation, where the representation of the vascular mask is bright compared to the representation of the medical component. Therein, the intensity or intensity distribution for the medical component may be determined by a corresponding intensity analysis as for the vascular mask.

With the described method, thus, the prerequisite is provided to calculate the ratio of component intensity and vascular tree intensity in real time (e.g., thus, continuously during fluoroscopy). Therein, considering previously defined threshold values (e.g., thresholds ascertained via a query and/or studies and/or calibration of the X-ray apparatus for a target ratio of the intensity desired in the overlay image in image areas (of the overlay image) with the vascular tree and image areas (of the overlay image) with the medical component to each other), a corresponding mixing algorithm or overlay algorithm for generating the overlay image may be adjusted. For example, weighting factors of the overlay algorithm may therefore be adjusted such that in an optimization method (e.g., the simplex optimization method or a gradient optimization method), the target value of an optimum target ratio of component intensity and vascular tree intensity is approximated. Therein, the standard deviation of respective analyzing methods or ascertaining methods may, for example, be used to then more accurately describe the target corridor of the parameterization of the optimization problem.

The method of one or more of the present embodiments allows achieving a constant image quality by the automatic adjustment of a defined contrast ratio between medical component and vascular mask in the overlay image (e.g., with respect to the overlay image in a roadmap mode (e.g., a subtracted roadmap mode). Thereby, manual adjustment becomes unnecessary; rather, the user may previously select which contrast ratio of component and vascular tree the user desires in the overlay image for the planned intervention, and the contrast ratio is adjusted for the user in any situations during fluoroscopy in real time via the method by the X-ray apparatus with an associated computing unit.

In one embodiment, in ascertaining the vascular mask intensity and/or the component intensity, a histogram of the respective intensity of the corresponding image areas is analyzed, and, for example, an average value respectively ascertained for the corresponding intensity is ascertained as the vascular mask intensity and/or component intensity. Therein, the histogram may be approached or approximated by a curve (e.g., a Gaussian curve), and the average value and/or a standard deviation of a corresponding distribution may be parameterized.

This has the advantage that the corresponding intensity is accurately ascertained, and thus, the contrast ratio may also be particularly well optimized.

In a further embodiment, segmenting the second X-ray image includes pre-selecting a coarse image area with the medical component, as well as segmenting based on a threshold value with selecting the image area with the medical component from the coarse image area. The coarse image area is a partial area of the second X-ray image and larger than the finally segmented and selected image area with the medical component.

This has the advantage that involving artifacts in the segmenting based on threshold value is avoided via pre-selection of the coarse image area. Computing capacity may thus be saved. Thus, the component intensity may overall be faster and more accurately determined.

Therein, it may be provided that the pre-selection is effected using at least one landmark present in the second X-ray image (e.g., one or more landmarks) and/or is effected using a location mask for the vascular tree.

This has the advantage that image areas that are far away from the vascular tree are recognized as such via the additional landmarks (e.g., due to known recorded anatomic correlations), and a template for the image areas relevant to fluoroscopy is provided by the location mask with a simple computing step. Thus, the accuracy of the method is again increased, and the required computational effort is reduced.

The location mask is generated depending on the vascular mask already generated within the scope of this method by capturing the first X-ray image and corresponding segmenting of the first X-ray image by the image area with the vascular tree and thus present. For example, the location mask may be generated depending on the vascular mask increased by a buffer zone. Thus, the location mask may include or be the vascular mask and/or a vascular mask increased by the buffer zone. The buffer zone may, for example, extend as a band with a preset thickness surrounding the vascular mask. Therein, the location mask may, for example, be a binary image of the vascular tree already segmented out (e.g., increased by the buffer zone). The assumption underlying this method act is that if a medical component is introduced into the patient, it is on the way in the vessels of the vascular tree. Thus, the inner mask including a safety distance may be applied to the second X-ray image as a buffer zone to consider movement and other displacements and there reduce the search space and consequently simplify the segmentation of the component image.

In a further embodiment, the second X-ray image is segmented using a learning-based pattern recognition algorithm, where the learning-based pattern recognition algorithm is, for example, used after pre-selecting the coarse image area.

This has the advantage that it may be provided that the pixel-identified pixels associated with the medical component actually belong to a contiguous medical component. In that the learning-based pattern recognition algorithm is employed after pre-selecting the coarse image area, valuable computing time may be saved.

In a further embodiment, the second X-ray image is repeatedly created, and the overlay image is repeatedly generated. Therein, the ratio of component intensity and vascular tree intensity is calculated repeatedly (e.g., continuously). This may be effected during the fluoroscopy.

This has the advantage that the overlay image is always automatically generated with an optimum contrast ratio automatically adjusted by the correspondingly used overlay or mixing algorithm.

In a further embodiment, the second X-ray image is repeatedly created, and the overlay image is repeatedly generated. Therein, a constant target ratio of the intensity of the overlay image in an image area with the vascular tree and the intensity of the overlay image in an image area with the component is preset for the overlay image, where the overlay image is generated depending on the target ratio and the calculated ratio.

This has the advantage that a preset (e.g., constant) contrast between the medical component and the vascular tree or the vascular mask may always automatically be adjusted in the overlay image. Therein, the target ratio may also be preset depending on capturing parameters of the X-ray apparatus for the second X-ray image or defined clinical situations (e.g., in dynamic manner). Thereby, the contrast in the overlay image is further optimized.

In one embodiment, the first X-ray image and/or the second X-ray image include an X-ray picture with multiple individual X-ray pictures or are based on an X-ray picture with multiple individual X-ray pictures (e.g., are composed of the multiple individual X-ray pictures), and segmenting the first X-ray image and/or the second X-ray image and/or ascertaining the intensity of the first X-ray image and/or the second X-ray image are effected consecutively for different areas of the vascular tree or the medical component in different individual X-ray images of the first and the second X-ray image, respectively. Segmenting or ascertaining the intensity may therefore be dynamically effected assuming a temporal propagation of the contrast agent flow (e.g., with a calculation of the bolus arrival time). The histogram or intensity analysis may therefore each be locally effected in sub-regions of the vessel tree and the medical component, respectively, to obtain the optimum calculation basis.

This has the advantage that by considering the temporal propagation of the contrast agent flow, particularly accurate images may be generated and complex anatomies are also well represented. Complex movement conditions, for example, of the medical component and a patient to each other may then also be considered by dynamically segmenting or ascertaining the intensity.

A further aspect relates to a medical X-ray apparatus (e.g., a C-arm X-ray apparatus) for creating a fluoroscopy. Therein, the medical X-ray apparatus includes a capturing unit for capturing a first X-ray image of a vascular tree as a vascular mask and for creating a second X-ray image of a medical component introduced in the vascular tree as a component image, as well as a computing unit for generating an overlay image with (e.g., from) the first X-ray image and with (e.g., from) the second X-ray image.

Therein, the computing unit is configured to segment the first X-ray image into at least one image area with the vascular tree and at least one image area without the vascular tree, and to ascertain an intensity of the first X-ray image for the image area with the vascular tree as a vascular mask intensity. Further, the computing unit is configured to segment the second X-ray image into an image area with the medical component and an image area without the medical component, and to ascertain an intensity of the second X-ray image for the image area with the medical component as a component intensity. The computing unit is also configured to calculate a ratio of component intensity and vascular tree intensity, and to generate the overlay image depending on the calculated ratio of vascular mask intensity and component intensity.

Advantages and advantageous embodiments of the medical X-ray apparatus correspond to advantages and advantageous embodiments of the described method.

The features and feature combinations mentioned above in the description, as well as the features and feature combinations mentioned below in the description of figures and/or shown in the figures alone are usable not only in the respectively specified combination, but also in other combinations without departing from the scope of the invention. Thus, implementations that are not explicitly shown in the figures and explained, but arise from and may be generated by separated feature combinations from the explained implementations, are also to be considered as encompassed and disclosed by the invention implementations and feature combinations that thus do not have all of the features of an originally formulated independent claim are also to be considered as disclosed. Moreover, implementations and feature combinations that extend beyond or deviate from the feature combinations set out in the relations of the claims (e.g., by the implementations set out above) are to be considered as disclosed.

BRIEF DESCRIPTION OF THE DRAWINGS

FIG. 1 shows one embodiment of a medical X-ray apparatus configured as a C-arm X-ray apparatus for creating a fluoroscopy.

DETAILED DESCRIPTION

As shown in FIG. 1, the medical X-ray apparatus 1 includes a capturing unit 2 for capturing a first X-ray image 3 of a vascular tree 4 as a vascular mask and for creating a second X-ray image 5 of a medical component 6 introduced into the vascular tree 4 (e.g., a wire) as a component image. The medical X-ray apparatus 1 also includes a computing unit 7 for creating an overlay image 8 from the first X-ray image 3 and the second X-ray image 5.

Therein, the computing unit 7 is formed to segment the first X-ray image 3 into at least one image area 9 with the vascular tree 4 and at least one, image area 10 (e.g., four image areas 10a to 10d) without the vascular tree 4. Therein, for the image area 9 with the vascular tree 4, an intensity of the first X-ray image 3 is ascertained as a vascular mask intensity by the computing unit 7.

The computing unit 7 is formed to segment the second X-ray image 6 into at least one image area 11 with the medical component 6 and at least one further image area 12 without the medical component, as well as to ascertain an intensity of the second X-ray image 5 for the image area 11 with the medical component 6 as a component intensity.

The computing unit 7 is configured to calculate a ratio of component intensity and vascular tree intensity and to generate the overlay image 8 depending on the calculated ratio of vascular mask intensity and component intensity. A corresponding overlay algorithm may, for example, be recorded in the computing unit 7. The first X-ray image 3 and the second X-ray image 6 depend on the calculated ratio and, for example, also depend on a preset target contrast or target ratio of the intensity of the overlay image 8 in the image areas with medical component and vascular tree, respectively. Thereby, an improved visibility of both the vascular tree 4 and the medical component 6 is achieved by an optimized contrast ratio, which is determined by the ratio of vascular mask intensity and component intensity.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for operating a medical X-ray apparatus in creating a fluoroscopy, the method comprising:
    capturing a first X-ray image, the first X-ray image being of a vascular tree as a vascular mask;
    segmenting the first X-ray image into at least one image area with the vascular tree and at least one image area without the vascular tree;
    ascertaining an intensity of the first X-ray image for the at least one image area with the vascular tree as a vascular mask intensity;
    creating a second X-ray image, the second X-ray image being of a medical component introduced into the vascular tree as a component image;
    segmenting the second X-ray image into an image area with the medical component and an image area without the medical component;
    ascertaining an intensity of the second X-ray image for the image area with the medical component as a component intensity;
    calculating a ratio of component intensity and the vascular tree intensity; and
    generating an overlay image with the first X-ray image and the second X-ray image depending on the calculated ratio of the component intensity and the vascular mask intensity.

2. The method of claim 1, wherein ascertaining the vascular mask intensity, ascertaining the component intensity, or ascertaining the vascular mask intensity and ascertaining the component intensity comprise:
    analyzing a histogram of the respective intensity of the corresponding image areas; and
    ascertaining an average value respectively ascertained for the intensity as the vascular mask intensity, the component intensity, or the vascular mask intensity and the component intensity.

3. The method of claim 1, wherein segmenting the second X-ray image comprises:
    pre-selecting a coarse image area with the medical component; and
    segmenting based on a threshold value with selecting the image area with the medical component.

4. The method of claim 3, wherein the pre-selection is effected using at least one landmark present in the second X-ray image, using a location mask for the vascular tree, or using a combination thereof.

5. The method of claim 4, wherein the location mask is generated depending on the vascular mask.

6. The method of claim 5, wherein the location mask is generated depending on the vascular mask increased by a buffer zone.

7. The method of claim 3, wherein the second X-ray image is segmented using a learning-based pattern recognition algorithm, and
    wherein the learning-based pattern recognition algorithm is used after pre-selecting the coarse image area.

8. The method of claim 1, wherein the second X-ray image is repeatedly created, the overlay image is repeatedly generated, and the ratio of the component intensity and the vascular tree intensity is repeatedly calculated.

9. The method of claim 8, wherein the vascular tree intensity is continuously calculated.

10. The method of claim 1, wherein the second X-ray image is repeatedly created, the overlay image is repeatedly generated, a constant target ratio of an intensity of the overlay image in an image area with the vascular tree and an intensity of the overlay image in an image area with the component is preset for the overlay image, and the overlay image is generated depending on the constant target ratio and the calculated ratio.

11. The method of claim 1, wherein the first X-ray image, the second X-ray image, or the first X-ray image and the second X-ray image include an X-ray picture with multiple individual X-ray images, and
    wherein segmenting the first X-ray image, the second X-ray image, or the first X-ray image and the second X-ray image, ascertaining the intensity of the first X-ray image, the second X-ray image, or the first X-ray image and the second X-ray image, or a combination thereof is consecutively effected for different areas of the vascular tree and the medical component, respectively, in different individual X-ray images of the first X-ray image and the second X-ray image, respectively.

12. A medical X-ray apparatus for creating a fluoroscopy, the medical X-ray apparatus comprising:
    a capturing unit configured to:
        capture a first X-ray image of a vascular tree as a vascular mask; and
        create a second X-ray image of a medical component introduced into the vascular tree as a component image; and
    a computer configured to:
        generate an overlay image with the first X-ray image and with the second X-ray image;
        segment the first X-ray image into at least one image area with the vascular tree and at least one image area without the vascular tree;
        ascertain an intensity of the first X-ray image for the image area with the vascular tree as a vascular mask intensity; and
        segment the second X-ray image into at least one image area with the medical component and at least one image area without the medical component; and
        ascertain an intensity of the second X-ray image for the image area with the medical component as a component intensity;
        calculate a ratio of the component intensity and the vascular tree intensity; and
        generate the overlay image depending on the calculated ratio of the component intensity and the vascular tree intensity.

13. The medical X-ray apparatus of claim 12, wherein the medical X-ray apparatus comprises a C-arm X-ray apparatus.

* * * * *